United States Patent
Behring et al.

(10) Patent No.: US 7,268,352 B2
(45) Date of Patent: Sep. 11, 2007

(54) APPARATUS AND METHOD FOR DETERMINING THE PROPORTION OF A SUBSTANCE IN A GAS SAMPLE USING AN INFRARED MEASURING INSTRUMENT

(75) Inventors: Rasmus Behring, Lubeck (DE); Peter Dreyer, Pansdorf (DE); Horst-Dieter Hattendorff, Bad Schwartau (DE); Bernd-Michael Dicks, Ratekau (DE); Hans Matthiessen, Bad Schwartau (DE)

(73) Assignee: Dragerwerk Artiengesellschaft (DE)

( * ) Notice: Subject to any disclaimer, the term of this patent is extended or adjusted under 35 U.S.C. 154(b) by 316 days.

(21) Appl. No.: 11/141,112

(22) Filed: Jun. 1, 2005

(65) Prior Publication Data

US 2005/0274893 A1 Dec. 15, 2005

(30) Foreign Application Priority Data

Jun. 11, 2004 (DE) .................. 10 2004 028 360

(51) Int. Cl.
*H02H 7/125* (2006.01)
*G01J 5/02* (2006.01)

(52) U.S. Cl. ...................... 250/343; 250/351
(58) Field of Classification Search ......... 250/343, 250/351, 339.01, 340, 341.1, 350; 356/51, 356/432, 437
See application file for complete search history.

(56) References Cited

U.S. PATENT DOCUMENTS 3,922,551 A * 11/1975 Williams ............... 250/343
4,817,013 A * 3/1989 Corenman et al. .......... 702/30
5,239,860 A * 8/1993 Harris et al. ............. 73/61.48

(Continued)

FOREIGN PATENT DOCUMENTS

| EP | 0 10 88 04 B1 | 9/1988 |
| EP | 0 584 519 | 11/1997 |
| JP | 0 228 7125 A | 11/1990 |

*Primary Examiner*—David Porta
*Assistant Examiner*—Faye Boosalis
(74) *Attorney, Agent, or Firm*—Nixon & Vanderhye PC (57) ABSTRACT

The invention relates to an apparatus and a method for improved correction of drift in an infrared measuring instrument. The measurement signal furnished by a thermal detector is split into a direct voltage component and an alternating voltage component. By means of calibration curves (24, 27), a calculated comparison variable $$T^{900}_{DC,korr}$$

is formed from a measured, averaged concentration value $$c^{900}_{ACI}.$$

The correction value ΔT for the drift correction is obtained from the difference between the corresponding measured size of the direct voltage component $$T^{900}_{DC}$$

and the comparison variable $$T^{900}_{DC,korr}.$$

6 Claims, 6 Drawing Sheets

U.S. PATENT DOCUMENTS 5,387,979 A * 2/1995 Brauer et al. ............... 356/435
5,506,685 A * 4/1996 Grasdepot ................... 356/409
6,114,700 A * 9/2000 Blades ....................... 250/343
6,133,573 A  10/2000 Bazin et al.

* cited by examiner

APPARATUS AND METHOD FOR DETERMINING THE PROPORTION OF A SUBSTANCE IN A GAS SAMPLE USING AN INFRARED MEASURING INSTRUMENT

CROSS-REFERENCES TO RELATED APPLICATIONS

This application is based on and incorporates herein by reference German Patent Application No. DE 102004028360.5 filed on Jun. 11, 2004.

BACKGROUND OF THE INVENTION

The invention relates to an apparatus and a method for determining the proportion of a substance in a gas sample using an infrared measuring instrument.

From European Patent Disclosure EP 584 519 B1, an apparatus and a method for measuring the concentration of a substance in a gas sample with an infrared measuring instrument has been disclosed. A radiation source, triggered by a modulated current, shines through the gas sample to be examined, and the measurement radiation is recorded by a measuring detector and a reference detector. The measurement and reference signals output by the respective detectors are composed of a dark signal, a direct voltage component, and an alternating voltage component. The dark signal is established as a substantially constant offset voltage, when the radiation source is darkened.

The direct voltage component and the alternating voltage component are each dependent on the measured concentration.

The ratio between the alternating voltage component and the direct voltage component is independent of the concentration, and is a function of only the degree of modulation of the radiation source.

The concentration of the substance is determined from the direct voltage component of the measurement signal, and the alternating voltage component of the reference signal is used for standardizing the direct voltage component of the measurement signal.

The known measuring instrument necessitates highly complicated circuitry to split up the measurement signal and the reference signal into the different voltage components. The measurement method is suitable only for detectors that have a defined dark signal, and only short-wave infrared radiation in the absorption range of carbon dioxide can be detected.

BRIEF DESCRIPTION OF THE INVENTION

The object of the invention is to disclose an apparatus and a method for improved drift correction of an infrared measuring instrument.

This object is attained with an apparatus for infrared-optical determination the concentration of a substance in a gas sample, having the following characteristics: a modulated radiation source; a thermal detector; a measurement chamber between the radiation source and the detector, as a measurement distance for recording the gas sample; means for splitting the measurement signal, furnished by the detector, into a direct voltage component and an alternating voltage component; means for forming averaged transmissions $$T_{DC}^{900}, T_{AC}^{900}$$

of the direct voltage component and of the alternating voltage component; calibration curves, for the functional relationship between transmission and concentration, associated individually with the transmissions of the direct voltage component and the transmissions of the alternating voltage component; and means for forming a correction value for the direct voltage component, by forming the correction value $\Delta T$ from the deviation of a comparison variable $$T_{DC,korr}^{900},$$

formed from the averaged alternating voltage component $$T_{ACI}^{900}$$

with the calibration curves, from the associated, averaged direct voltage component $$T_{DCI}^{900}.$$

The object for the method is also attained with a method for determining the concentration of a substance in a gas sample with an infrared measuring instrument, which includes a thermal detector, a modulated radiation source, and a measurement distance between the detector and the radiation source, characterized by the following steps: splitting the measurement signal, furnished by the detector, into a direct voltage component and an alternating voltage component; from the alternating voltage component, using a first calibration curve, ascertaining a first, averaged concentration value $$c_{ACI}^{900};$$

from the first concentration value, using a calibration curve, determining a calculated comparison variable $$T_{DC,korr}^{900}$$

of the direct voltage component; and from the deviation of the calculated comparison variable $$T_{DC,korr}^{900}$$

from the corresponding size of the measured direct voltage component $$T^{900}_{DCl},$$

forming a drift signal $\Delta T$, $U_{Drift}$ for correcting the direct voltage component.

The advantage of the invention is essentially that as the radiation receiver, a thermal detector is used which is also suitable for recording longer-wave infrared radiation to detect anesthesia gases. Such thermal detectors, however, do not have any defined dark signal, since thermal emissions affect the dark signal. For evaluating the measurement signal, this measurement signal is split up into a direct voltage component and an alternating voltage component; the alternating voltage component is obtained from the modulation of the radiation source. In the process of a preceding calibration, separate calibration curves for known substance concentrations are recorded for the direct voltage signal and the alternating voltage signal. In the ideal case, in an ensuing concentration measurement, the concentrations ascertained from the direct voltage component and the alternating voltage component will match. If the two concentrations do not match, then it is likely that the dark signal, which is superimposed on the direct voltage signal, has changed. From this assumption, it is possible to calculate a correction signal for the transmission.

A detector converts the light output $\Phi$ into a voltage $U(c)$, which is easy to evaluate electronically. When the light source is switched off, the thermal detector used according to the invention also furnishes a voltage $U_{dunkel}$, which must be subtracted from the measured voltage in order to obtain an equivalent voltage for the variable light output. Accordingly, in determining the initial light output $\Phi_0$, the dark voltage $U_{dunkel}$ must be subtracted from the voltage in the absence of the measurement gas $U_{hell}$. Lambert-Beer's law can be applied to these measured voltages:

$$U(c) - U_{dunkel} = (U_{hell} - U_{dunkel}) \cdot \exp(-R_0 \cdot c) \quad (1)$$

The ratio of the light output $\Phi$ to the initial light output $\Phi_0$ corresponds to the transmission T through the gas:

$$T = \frac{\Phi}{\Phi_0} = \frac{U(c) - U_{dunkel}}{U_{hell} - U_{dunkel}} = \exp(-R_0 \cdot c) \quad (2)$$

Alternatively to the reference points chosen here for the physical transmission, that is, $U_{hell}$ and $U_{dunkel}$, values can also be taken from other reference points with defined concentrations.

The measured voltages $U(c)$ can be converted into a transmission using Equation 2 for the alternating signal component (AC) and the direct signal component (DC). Since because of the filter properties, the transmission does not return to zero at even very high concentrations, the exponential function of Lambert-Beer's law has been provided with a preliminary factor A. Since the transmission in the absence of anesthesia gas should be 1, however, an additive constant 1−A is introduced. The result is the following general relationship for the transmission:

$$T = (1-A) + A \cdot \exp(-R_0 \cdot c) \quad (3)$$

The radiation source is operated at alternating current at 118 Hz. Because of the thermal inertia of the emitter, this light at the measurement wavelengths emits with a small alternating component and a large direct component. Since the radiation source is excited from outside, the information about the frequency and the period length is available.

This allows the measurement signal to be split, with the aid of the lock-in process, including averaging over 900 periods, into an alternating voltage signal $$U^{900}_{AC}$$

and a direct voltage signal $$U^{900}_{DC},$$

which for the sake of comparability is also averaged over 900 periods. Both voltages contain information about the concentration of the measurement gas, since both the alternating voltage component and the direct voltage component of the light are influenced by the gas. A concentration can therefore be determined from both voltages. If both concentrations match within a defined confidence range, then it can be assumed that no drift has occurred. If not, drift is thus detected, and hence it is possible to warn the user.

The foundation of the drift correction is the combination of information from the direct voltage component and the alternating voltage component of the light detected. If the concentrations ascertained from the direct voltage signal and the alternating voltage signal do not match, then it is likely that the direct voltage signal has drifted, relative to the dark signal $U_{DC,dunkel}$ by the voltage $U_{Drift}$, in accordance with Equation (2):

$$U_{DC,dunkel}(\text{neu}) = U_{DC,dunkel} + U_{Drift} \quad (4)$$

By means of this assumption, it is possible to ascertain a drift voltage $U_{Drift}$. Equation (2) for calculating the transmission is modified to correct for drift for the direct signal:

$$\begin{aligned} T^{900}_{DC,korr} &= \frac{U^{900}_{DC} - U_{Drift} - U_{DC,dunkel}}{U_{DC,hell} - U_{DC,dunkel}} \\ &= T^{900}_{DC} - \frac{U_{Drift}}{U_{DC,hell} - U_{DC,dunkel}} \\ &= T^{900}_{DC} - \Delta T \end{aligned} \quad (5)$$

Since the "true" averaged concentration $$c^{900}_{AC}$$

is known from the alternating signal (AC), it is simultaneously possible, by way of Equation (3), to draw a conclusion about the transmission $$T^{900}_{DC,korr}.$$

By equating it with Equation (5), the drift voltage can be calculated:

$$U_{Drift} = \qquad (6)$$
$$(T_{DC}^{900} - (1 - A_{DC}) - A_{DC} \cdot \exp(-R_{0,DC} \cdot c_{AC}^{900})) \cdot (U_{DC,hell} - U_{DC,dunkel})$$

The drift voltage ascertained in this way represents not its current value, but rather its average value over the last 900 periods. The drift voltage $U_{Drift}$ (or selectively the transmission difference $\Delta T$) can, however, be used for correcting the quick direct signal evaluation. With the aid of Equation (5), modified for the quick determination of the concentration, the corrected transmission $T_{DC,korr}$ is calculated:

$$T_{DC,korr} = \frac{U_{DC} - U_{Drift} - U_{DC,dunkel}}{U_{DC,hell} - U_{DC,dunkel}} = T_{DC} - \Delta T \qquad (7)$$

From this transmission, with the aid of Equation (3), or the following equation $$T = (1-A) + A \cdot \exp(R_1 \cdot c + R_2 \cdot c^2 + R_3 \cdot c^3) \qquad (8)$$

It is possible to draw a conclusion about the corrected concentration for the $CO_2$ channel, in the form of a third-degree polynomial having the constants $R_1$, $R_2$ and $R_3$.

BRIEF DESCRIPTION OF THE DRAWINGS

These and other objects and advantages of this invention, will be more completely understood and appreciated by careful study of the following more detailed description of the presently preferred exemplary embodiments of the invention taken in conjunction with the accompanying drawings, in which.

DETAILED DESCRIPTION OF THE INVENTION

Figure 1:
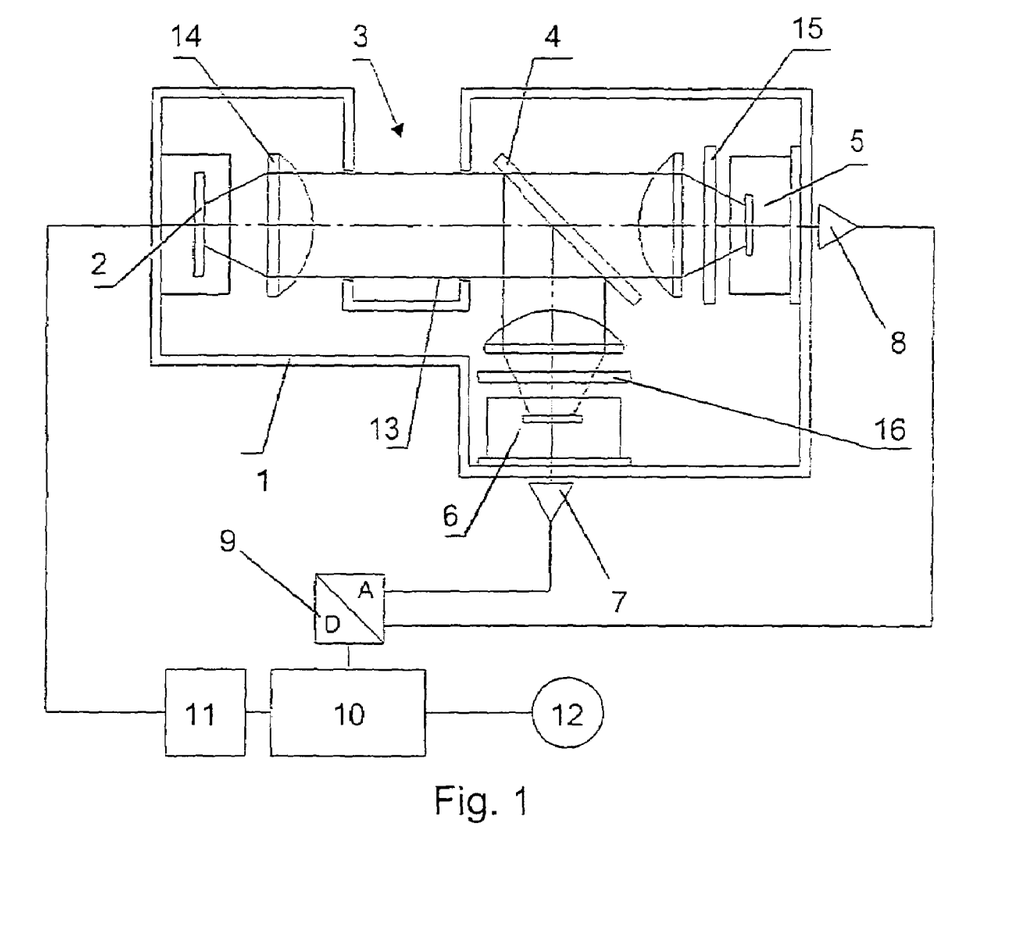
FIG. 1 is an infrared measuring instrument.

FIG. 1 schematically shows the layout of an infrared measuring instrument 1, which comprises a radiation source 2, a measurement chamber 3 for the gas sample to be examined, a beam splitter 4, a thermal measurement detector 5, and a thermal reference detector 6. The measurement signals of the detectors 5, 6, via preamplifiers 7, 8 and an analog/digital converter 9, reach an evaluation unit 10. A signal transducer 11 that triggers the radiation source 2 and a display unit 12 are also connected to the evaluation circuit 10. The infrared radiation 13 emitted by the radiation source 2 travels via a collimating lens 14 to reach the measurement chamber 3, where the gas sample to be examined is located. Downstream of the measurement chamber 3, the infrared radiation 13 is deflected by means of the beam splitter 4 to the detectors 5, 6 via filters 15, 16.

Figure 2:
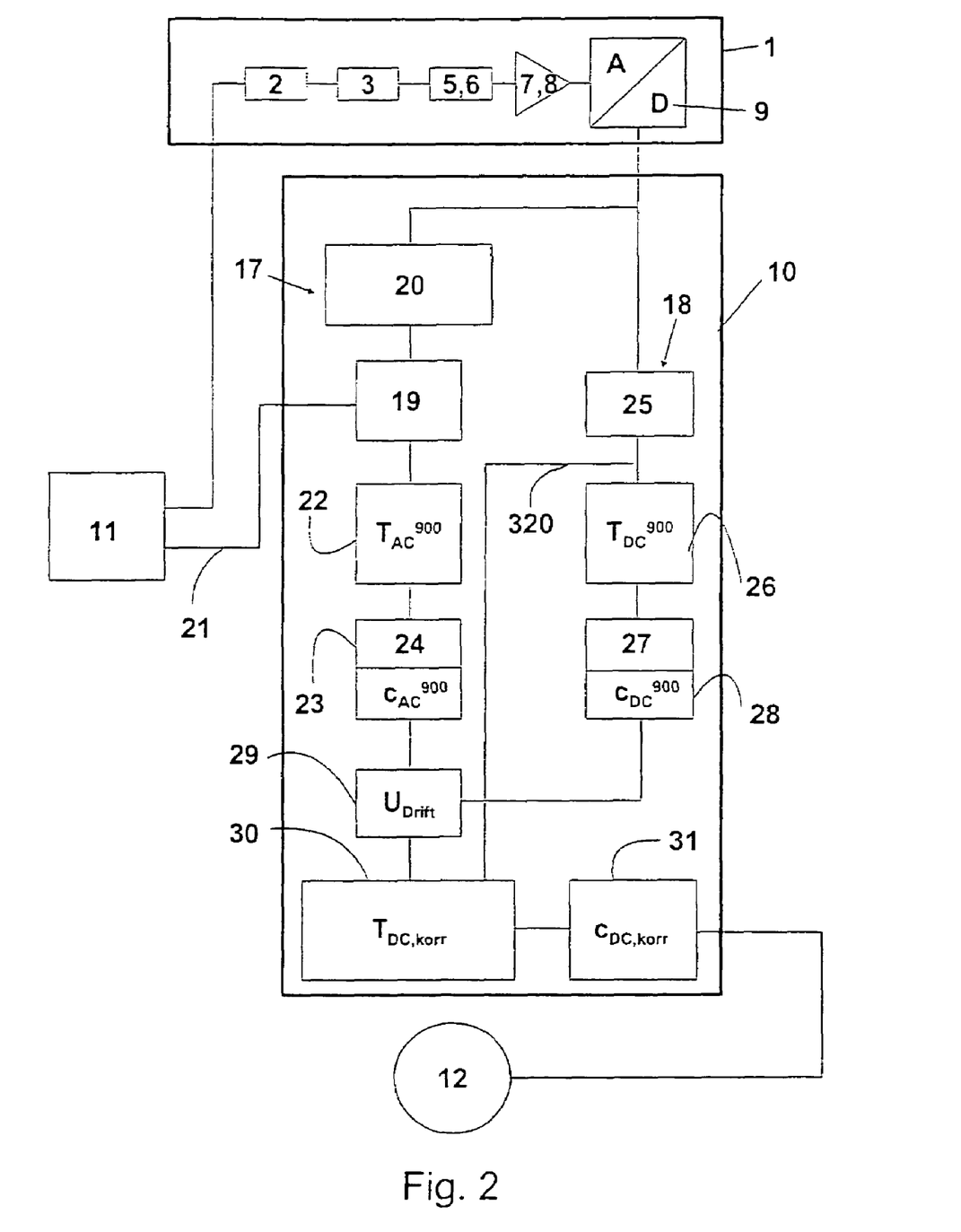
FIG. 2 is a detailed structure of the evaluation circuit of the infrared measuring instrument of FIG. 1.

FIG. 2 illustrates an exemplary embodiment for the detailed structure of the measurement value circuit 10 for the infrared measuring instrument 1.

The signal transducer 11 triggers the radiation source 2 with an alternating voltage component. The detectors 5, 6 furnish a measurement signal, which comprises a direct voltage component and an alternating voltage component. The evaluation circuit 10 includes separate channels for the voltage components, in the form of a first evaluation channel 17 for the alternating voltage component and a second evaluation channel 18 for the direct voltage component. The first evaluation channel 17 includes a lock-in amplifier 19 for phase-sensitive rectification and averaging of the alternating voltage component, preceded by a filter 20 for filtering out the direct component. For synchronizing the phase-sensitive rectification with the trigger signal for the radiation source 2, the lock-in amplifier receives a reference signal from the signal transducer 11 over the line 21. In an evaluation block 22 at the output of the lock-in amplifier 19, there is a sliding averaged value for the transmission $$T_{AC}^{900}.$$

After that, in an evaluation block 23, the concentration $$c_{AC}^{900}$$

is calculated, by means of a first calibration curve 24, for the transmission of the alternating voltage component $$T_{AC}^{900}.$$

In the second evaluation channel 18, downstream of an evaluation block 25 for averaging over one period, a sliding average of the transmission $$T_{DC}^{900}$$

over 900 periods is calculated in a downstream evaluation block 26. With a second calibration curve for the transmission of the direct voltage component $$T_{DC}^{900},$$

the concentration $$c_{DC}^{900}$$

is ascertained in an evaluation block 28. By comparison of the concentrations $$c_{AC}^{900} \text{ and } c_{DC}^{900},$$

the drift voltage, Equation (8), is obtained in an evaluation block 29.

In an evaluation block 30, the corrected transmission of the direct voltage component $T_{DC,korr}$ is ascertained, with Equation (7), taking into account the drift voltage and unaveraged direct voltage component $T_{DC2}$. In the evaluation block 31, the corrected concentration $c_{DC,korr}$ is calculated, which is output via the display unit 12. The unaveraged direct voltage component $T_{DC2}$ reaches the evaluation block 30 over a line 320.

Figure 3:
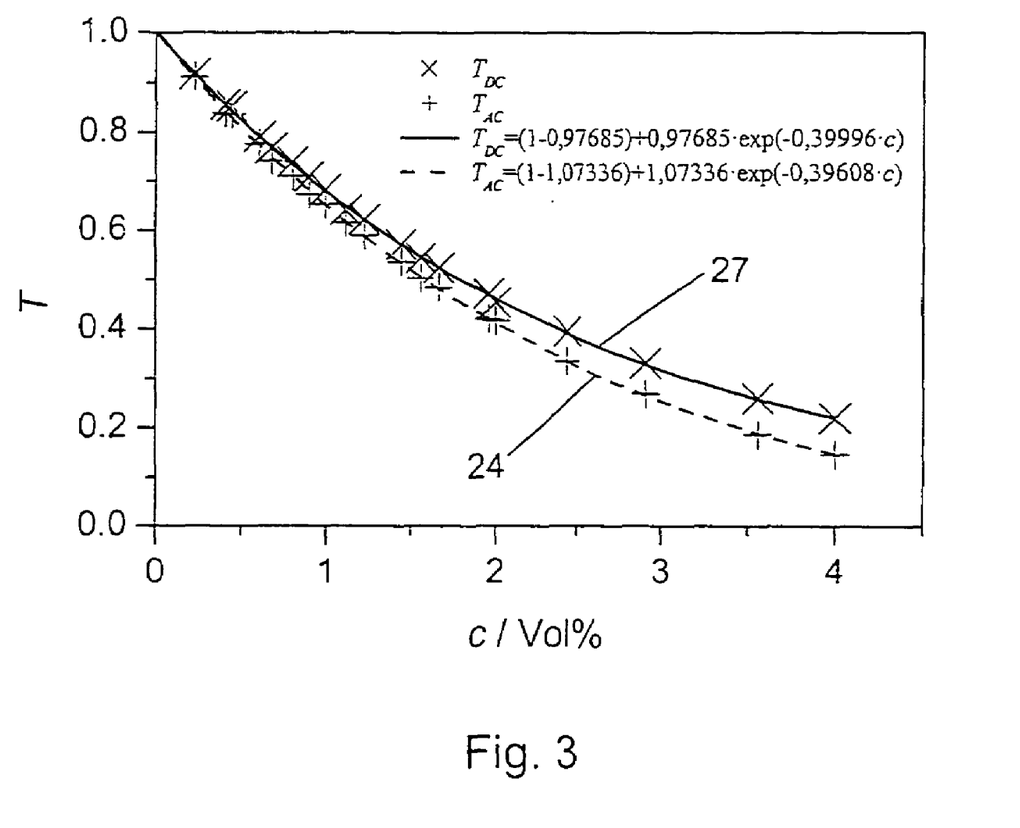
FIG. 3 illustrates calibration curves for anesthesia gases.

FIG. 3 illustrates the calibration curves 24, 27, where T=T(c) for the transmission of the alternating voltage component $T_{AC}$ and the direct voltage component $T_{DC}$ for typical anesthesia gas concentrations. The general relationship for the transmission is obtained from Equation (3). FIG. 3 shows individual measurement points, which have been recorded synchronously in the measurement chamber 3 for known anesthesia gas concentrations. The calibration curves 24, 27 differ essentially in the constant A, which can be ascribed to the fact that the thermal detectors 5, 6 in AC operation see a different background from that in DC operation.

Figure 4:
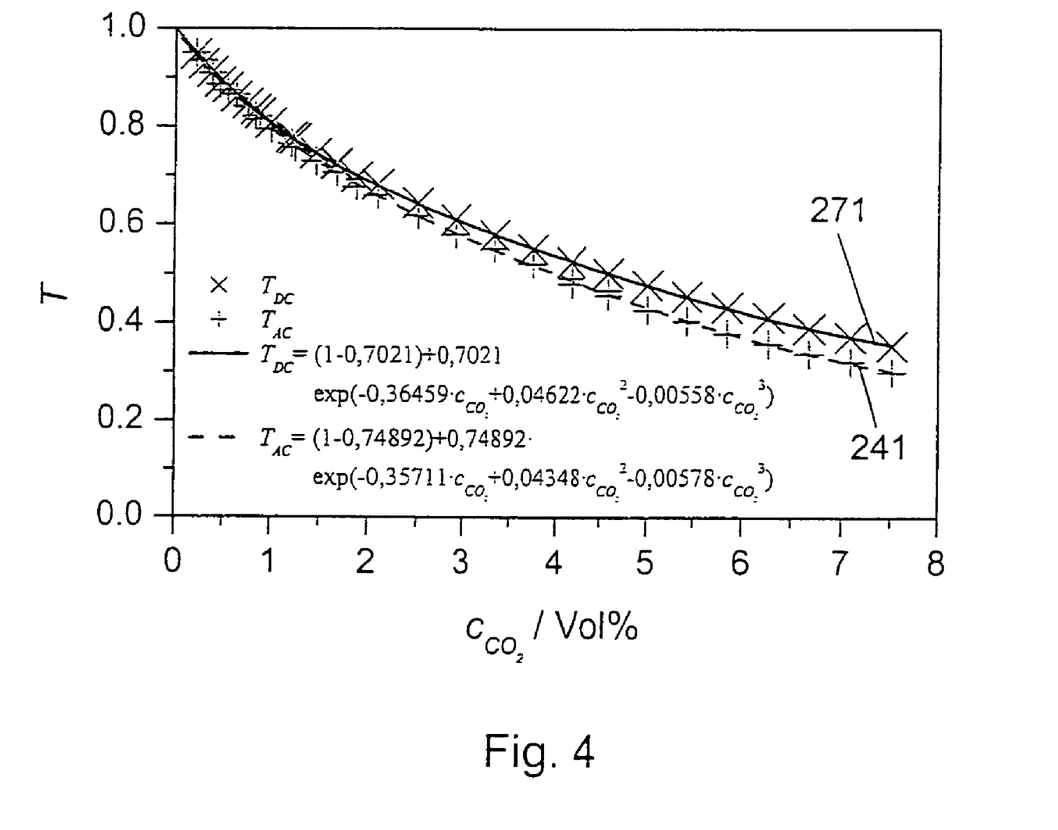
FIG. 4 illustrates calibration curves for carbon dioxide.

If a second gas component, such as $CO_2$, is to be detected with the infrared measuring instrument 1 in parallel, then the evaluation circuit 10 is expanded with additional evaluation channels, which separately evaluate the AC and DC components. For $CO_2$, separate calibration curves 241, 271 must be recorded, as can be seen from FIG. 4. The calibration curve 271 refers to the transmission of the direct component $T_{DC}$, and the calibration curve 241 refers to the alternating component.

Figure 5:
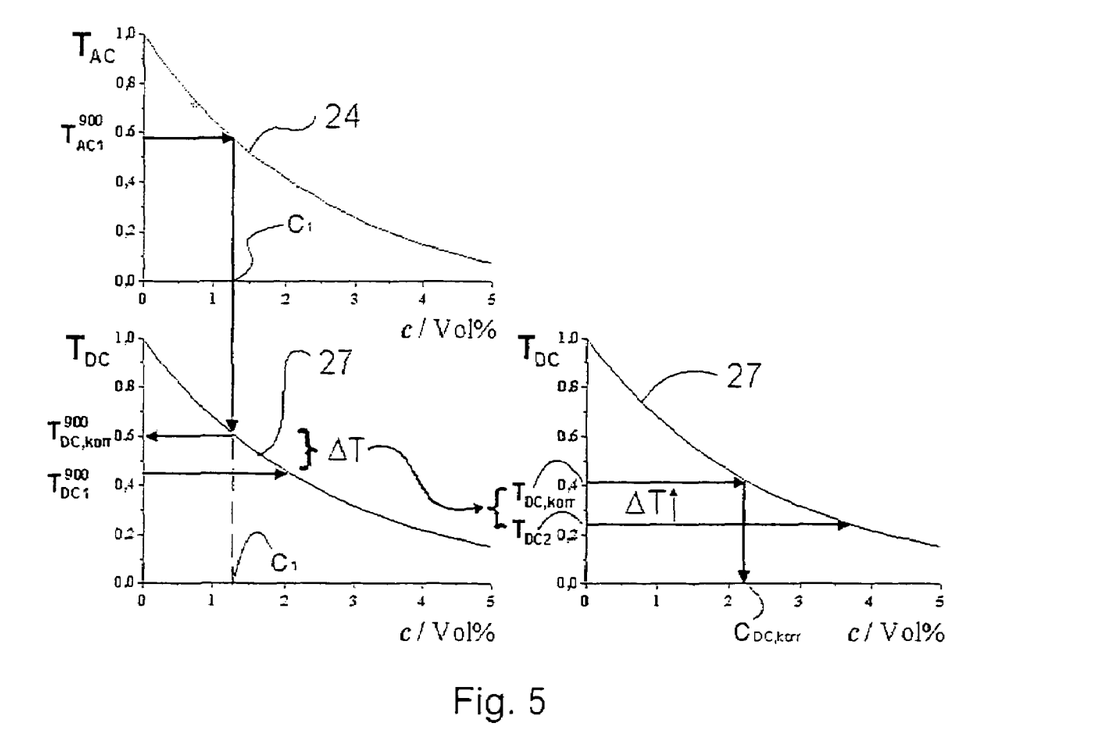
FIG. 5 is a graph illustrating an evaluation method.

FIG. 5 illustrates an alternative evaluation method, in which the drift correction is performed not with a drift voltage $U_{Drift}$ but rather with a transmission difference $\Delta T$. A measured, averaged transmission $$T_{AC1}^{900}$$

of the alternating voltage component, with the first calibration curve 24, yields the concentration value $C_1$. From $C_1$, the associated transmission $$T_{DC,korr}^{900}$$

is obtained by means of the second calibration curve 27.

The measured, averaged transmission of the direct voltage component is $$T_{DC1}^{900}.$$

Between the measured transmission $$T_{DC1}^{900}$$

and the transmission $$T_{DC,korr}^{900},$$

a transmission difference $\Delta T$ results, which can be ascribed to an additive drift of the direct voltage component. Without drift, $\Delta T$ would equal zero, or in other words $$T_{DC1}^{900} = T_{DC,korr}^{900}.$$

A measured, unaveraged transmission $T_{DC2}$ of the direct voltage component must be corrected by $\Delta T$ if the true concentration $C_{DC,korr}$ is to be obtained. The transmission difference $\Delta T$, determined from averaged transmissions $$T_{AC1}^{900}, T_{DC1}^{900}$$

by means of the characteristic curves 24, 27, is used for correcting the transmission a measured, unaveraged transmission $T_{DC2}$.

Figure 6:
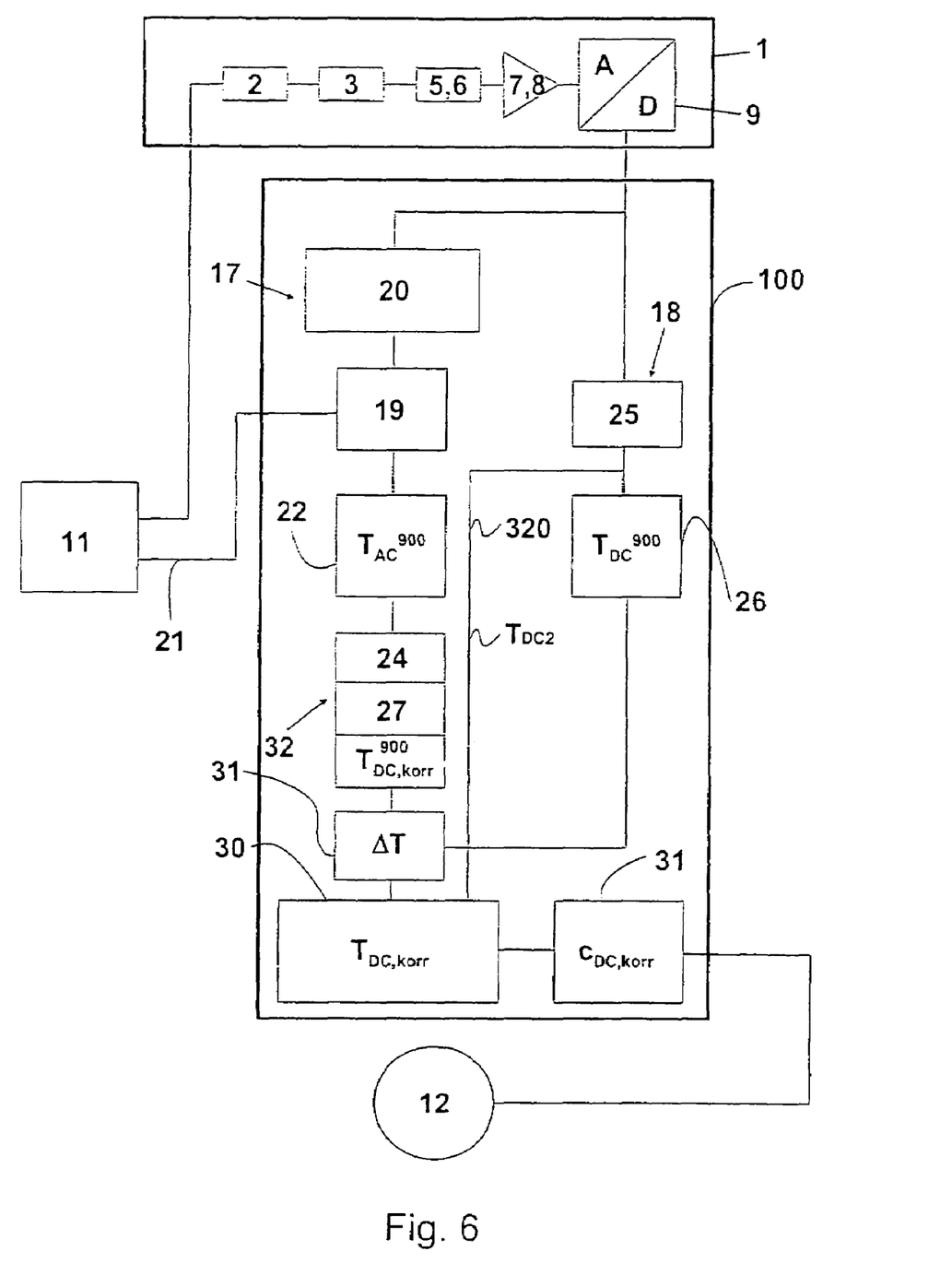
FIG. 6 is a detailed structure of the evaluation circuit of FIG. 5.

FIG. 6 shows the detailed structure of an evaluation unit 100 corresponding to the evaluation method of FIG. 5. Identical components are identified by the same reference numerals as in FIG. 2.

The linking of the calibration curves 24, 27 for ascertaining an averaged correction value for the transmission $$T_{DC,korr}^{900}$$

are summarized in an evaluation block 32. The unaveraged transmission $T_{DC2}$ is transmitted from the output of the evaluation block 25 to the evaluation block 30 over the line 320.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

Abbreviations Used:

A Precursor factor in Lambert-Beer's law
$R_0$ Positive, concentration-independent part of the exponent in Lambert-Beer's law
$R_1, R_2, R_3$ Coefficients of the third-degree polynomial in the exponent of Lambert-Beer's law, modified for $CO_2$
$\Phi_0$ Initial light output (before attenuation by gas absorption)<
$\Phi$ Light output (after attenuation by gas absorption)
$U_{hell}$ Detector voltage in the absence of the gas being measured
$U_{dunkel}$ Detector voltage with emitter switched off
$U_{DC}$ Direct voltage component of detector signal
$U_{DC}^{900}$ Direct voltage component of the detector signal, averaged over 900 periods
$U_{DC,hell}$ Direct voltage component of the detector signal in the absence of the gas being measured $U_{DC,dunkel}$ Direct voltage component of the detector signal with the emitter switched off
$U_{Drift}$ Additive drift voltage
c Concentration
U(c)) Concentration-dependent detector voltage
$U_{AC}$ Alternating voltage component of the detector signal
$U_{AC}^{900}$ Alternating voltage component of the detector signal, averaged over 900 periods
T Transmission
$T_{DC}$ Transmission of the constant light
$T_{DC}^{900}$ Transmission of the constant light, averaged over 900 periods
$T_{DC,korr}^{900}$ Corrected transmission of the direct light, averaged over 900 periods
$T_{AC}$ Transmission of the alternating light
$T_{AC}^{900}$ Transmission of the alternating light, averaged over 900 periods
$c_{AC}^{900}$ Concentration determined from $T_{AC}^{900}$
$c_{DC,korr}$ Corrected concentration of the direct light
$\Delta T$ Correction value of the transmission
$T_{DC2}$ Unaveraged direct voltage component of the transmission

What is claimed is:

1. An apparatus for infrared-optical determination of the concentration of a substance in a gas sample, having the following characteristics:
 a modulated radiation source;
 a thermal detector;
 a measurement chamber between the radiation source and the detector, as a measurement distance for recording the gas sample;
 means for splitting the measurement signal, furnished by the detector, into a direct voltage component and an alternating voltage component;
 means for forming averaged transmissions $$T_{DC}^{900}, T_{AC}^{900}$$

of the direct voltage component and of the alternating voltage component;
 calibration curves, for the functional relationship between transmission and concentration, associated individually with the transmissions of the direct voltage component and the transmissions of the alternating voltage component; and
 means for forming a correction value for the direct voltage component, by forming the correction value $\Delta T$ from the deviation of a comparison variable $$T_{DC,korr}^{900},$$

formed from the averaged alternating voltage component $$T_{ACI}^{900}$$

with the calibration curves, from the associated, averaged direct voltage component $$T_{DCI}^{900}.$$

2. The apparatus according to claim 1, characterized in that the correction value $\Delta T$ serves to correct an unaveraged direct voltage component $T_{DC2}$.

3. The apparatus according to claim 1, characterized in that as an alternative to the transmission difference $\Delta T$ for correction, a concentration difference is used.

4. A method for determining the concentration of a substance in a gas sample with an infrared measuring instrument, which includes a thermal detector, a modulated radiation source, and a measurement distance between the detector and the radiation source, characterized by the following steps:
 splitting the measurement signal, furnished by the detector, into a direct voltage component and an alternating voltage component;
 from the alternating voltage component, using a first calibration curve, ascertaining a first, averaged concentration value $$c_{ACI}^{900};$$

from the first concentration value, using a calibration curve, determining a calculated comparison variable $$T_{DC,korr}^{900}$$

of the direct voltage component;
 from the deviation of the calculated comparison variable $$T_{DC,korr}^{900}$$

from the corresponding size of the measured direct voltage component $$T_{DCI}^{900},$$

forming a drift signal $\Delta T$, $U_{Drift}$ for correcting the direct voltage component.

5. The method according to claim 4, characterized in that the drift signal is used for correcting an unaveraged direct voltage component $T_{DC2}$.

6. The apparatus according to claim 2, characterized in that as an alternative to the transmission difference $\Delta T$ for correction, a concentration difference is used.

* * * * *